United States Patent
Soltz et al.

(10) Patent No.: US 10,476,432 B2
(45) Date of Patent: Nov. 12, 2019

(54) HIGH THROUGHPUT SYSTEM FOR PHOTOVOLTAIC UV DEGRADATION TESTING

(71) Applicant: SUNPOWER CORPORATION, San Jose, CA (US)

(72) Inventors: David Aitan Soltz, Mountain View, CA (US); Yoann Buratti, Santa Clara, CA (US); Xiuwen Tu, San Jose, CA (US); Ryan Manuel Lacerda, El Granada, CA (US); Taiqing Qiu, Los Gatos, CA (US)

(73) Assignee: SunPower Corporation, San Jose, CA (US)

( * ) Notice: Subject to any disclaimer, the term of this patent is extended or adjusted under 35 U.S.C. 154(b) by 253 days.

(21) Appl. No.: 15/395,576

(22) Filed: Dec. 30, 2016

(65) Prior Publication Data
US 2018/0041165 A1    Feb. 8, 2018

Related U.S. Application Data

(60) Provisional application No. 62/371,696, filed on Aug. 5, 2016.

(51) Int. Cl.
| H02S 50/15 | (2014.01) |
| G01N 21/64 | (2006.01) |
| H01L 31/18 | (2006.01) |
| G01N 21/95 | (2006.01) |

(52) U.S. Cl.
CPC ......... *H02S 50/15* (2014.12); *G01N 21/6489* (2013.01); *G01N 21/9501* (2013.01); *H01L 31/18* (2013.01)

(58) Field of Classification Search
CPC ............... H02S 50/15; G01N 21/9501; G01N 21/6489; H01L 31/18
USPC .................... 324/761.01, 537, 500
See application file for complete search history.

(56) References Cited

U.S. PATENT DOCUMENTS

| 6,617,972 B2* | 9/2003 | Takarada ........... G08B 21/0484 324/538 |
| 8,779,729 B2* | 7/2014 | Shiraishi ............... G06F 1/3212 320/155 |
| 10,230,329 B2* | 3/2019 | Tu ............................ H02S 50/15 |
| 2010/0166600 A1* | 7/2010 | Barak ........................ C02F 1/32 422/24 |
| 2015/0325715 A1* | 11/2015 | Sun .................... H01L 31/02242 136/256 |
| 2016/0329864 A1 | 11/2016 | Tu et al. |

* cited by examiner

*Primary Examiner* — Giovanni Astacio-Oquendo
(74) *Attorney, Agent, or Firm* — Schwabe, Williamson & Wyatt, P.C.

(57) ABSTRACT

High throughput systems for photovoltaic UV degradation testing of solar cells, and methods of testing for UV degradation of solar cell during manufacture, are described herein. In an example, a high throughput solar cell testing apparatus includes a plurality of real time ultra-violet (RTUV) testing modules. Each of the RTUV testing modules includes an ultra-violet (UV) light source, an optics assembly for focusing light from the UV light source on a sample area, and a detector for receiving photoluminescence energy from the sample area. The high throughput solar cell testing apparatus also includes an acquisition and control assembly coupled to the plurality of RTUV testing modules.

20 Claims, 5 Drawing Sheets

HIGH THROUGHPUT SYSTEM FOR PHOTOVOLTAIC UV DEGRADATION TESTING

CROSS-REFERENCE TO RELATED APPLICATIONS

This application claims the benefit of U.S. Provisional Application No. 62/371,696, filed on Aug. 5, 2016, the entire contents of which are hereby incorporated by reference herein.

TECHNICAL FIELD

Embodiments of the present disclosure are in the field of renewable energy and, in particular, high throughput systems for photovoltaic UV degradation testing of solar cells, and methods of testing for UV degradation of solar cell during manufacture.

BACKGROUND

Photovoltaic cells, commonly known as solar cells, are well known devices for direct conversion of solar radiation into electrical energy. Generally, solar cells are fabricated on a semiconductor wafer or substrate using semiconductor processing techniques to form a p-n junction near a surface of the substrate. Solar radiation impinging on the surface of, and entering into, the substrate creates electron and hole pairs in the bulk of the substrate. The electron and hole pairs migrate to p-doped and n-doped regions in the substrate, thereby generating a voltage differential between the doped regions. The doped regions are connected to conductive regions on the solar cell to direct an electrical current from the cell to an external circuit coupled thereto.

Efficiency is an important characteristic of a solar cell as it is directly related to the capability of the solar cell to generate power. Likewise, efficiency in producing solar cells is directly related to the cost effectiveness of such solar cells. Accordingly, techniques for increasing the efficiency of solar cells, or techniques for increasing the efficiency in the manufacture of solar cells, are generally desirable. Some embodiments of the present disclosure allow for increased solar cell manufacture efficiency by providing novel processes for monitoring the fabrication of solar cell structures.

DETAILED DESCRIPTION

Figure 1:
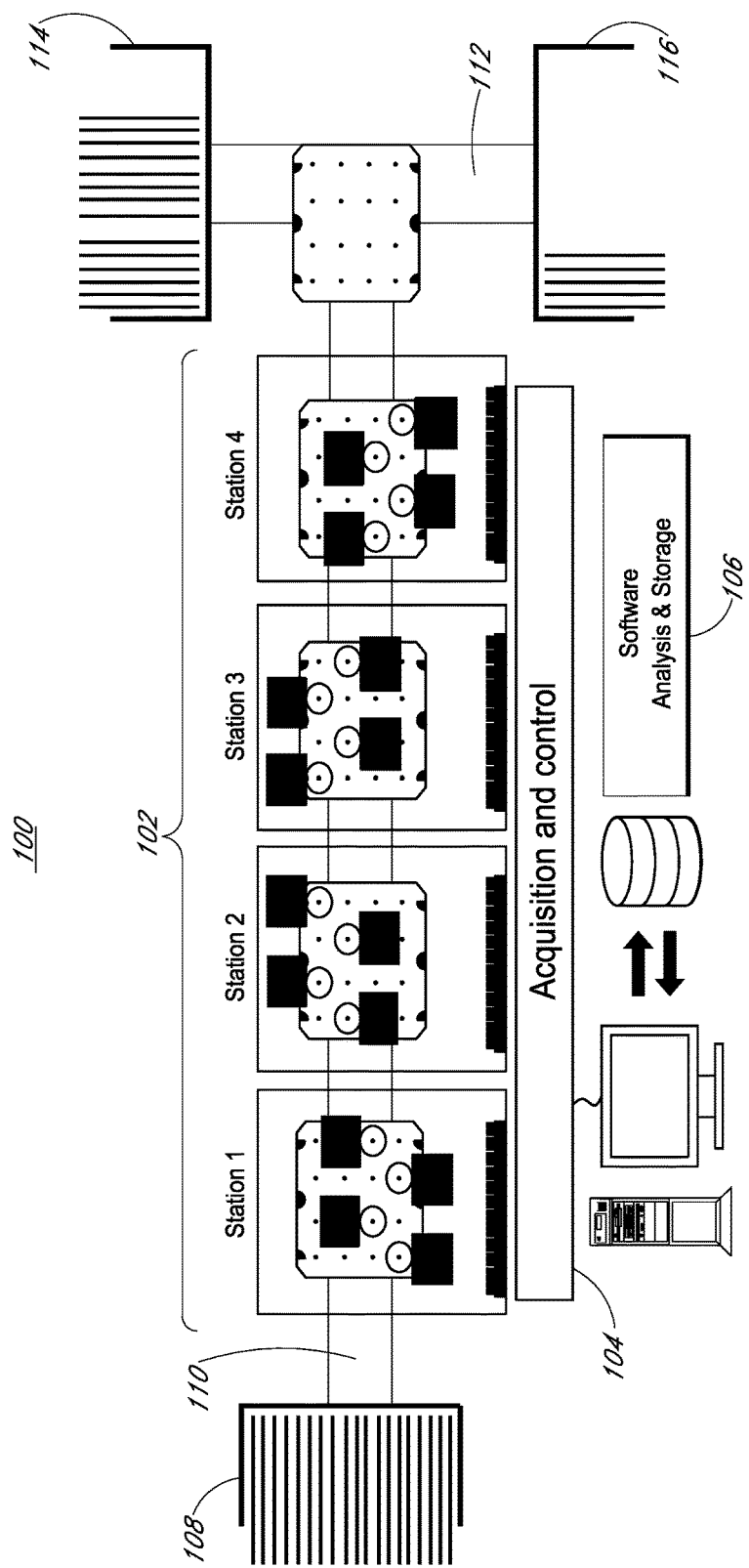
FIG. 1 illustrates a schematic of a high throughput solar cell testing apparatus, in accordance with an embodiment of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

Terminology. The following paragraphs provide definitions and/or context for terms found in this disclosure (including the appended claims):

"Comprising." This term is open-ended. As used in the appended claims, this term does not foreclose additional structure or steps.

"Configured To." Various units or components may be described or claimed as "configured to" perform a task or tasks. In such contexts, "configured to" is used to connote structure by indicating that the units/components include structure that performs those task or tasks during operation. As such, the unit/component can be said to be configured to perform the task even when the specified unit/component is not currently operational (e.g., is not on/active). Reciting that a unit/circuit/component is "configured to" perform one or more tasks is expressly intended not to invoke 35 U.S.C. § 112, sixth paragraph, for that unit/component.

"First," "Second," etc. As used herein, these terms are used as labels for nouns that they precede, and do not imply any type of ordering (e.g., spatial, temporal, logical, etc.). For example, reference to a "first" solar cell does not necessarily imply that this solar cell is the first solar cell in a sequence; instead the term "first" is used to differentiate this solar cell from another solar cell (e.g., a "second" solar cell).

"Coupled"—The following description refers to elements or nodes or features being "coupled" together. As used herein, unless expressly stated otherwise, "coupled" means that one element/node/feature is directly or indirectly joined to (or directly or indirectly communicates with) another element/node/feature, and not necessarily mechanically.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import.

"Inhibit" —As used herein, inhibit is used to describe a reducing or minimizing effect. When a component or feature is described as inhibiting an action, motion, or condition it may completely prevent the result or outcome or future state completely. Additionally, "inhibit" can also refer to a reduction or lessening of the outcome, performance, and/or effect which might otherwise occur. Accordingly, when a component, element, or feature is referred to as inhibiting a result or state, it need not completely prevent or eliminate the result or state.

High throughput systems for photovoltaic UV degradation testing of solar cells, and methods of testing for UV degradation of solar cell during manufacture, are described herein. In the following description, numerous specific details are set forth, such as specific tooling configurations, in order to provide a thorough understanding of embodiments of the present disclosure. It will be apparent to one skilled in the art that embodiments of the present disclosure may be practiced without these specific details. In other instances, well-known fabrication techniques, such as emitter region fabrication techniques, are not described in detail in order to not unnecessarily obscure embodiments of the present disclosure. Furthermore, it is to be understood that the various embodiments shown in the figures are illustrative representations and are not necessarily drawn to scale.

Disclosed herein are solar cell testing apparatuses. In one embodiment, a high throughput solar cell testing apparatus includes a plurality of real time ultra-violet (RTUV) testing modules. Each of the RTUV testing modules includes an ultra-violet (UV) light source, an optics assembly for focusing light from the UV light source on a sample area, and a detector for receiving photoluminescence energy from the sample area. The high throughput solar cell testing apparatus also includes an acquisition and control assembly coupled to the plurality of RTUV testing modules.

In another embodiment, a solar cell testing apparatus includes a first narrowband light source configured to induce photonic degradation to a solar cell. The inducing includes applying light of a first wavelength to the solar cell. A second narrowband light source is included for applying light of a second wavelength to the solar cell. The second wavelength is greater than the first wavelength. A detector is included and is configured to measure photoluminescence induced from the applied light of the first wavelength. A sheet resistance measurement module is included and is configured to measure a local resistance of a region of the solar cell. An electronic system is included and is configured to monitor the photonic degradation of the solar cell from the photoluminescence measurement, and is configured to monitor the local resistance of the region of the solar cell.

Also disclosed herein are methods for testing solar cells. In one embodiment, a method for testing a solar cell involves applying a first light to a sample region of a solar cell or a partially fabricated solar cell to induce a photonic degradation in the sample region. The method also involves applying a second light to the sample region to induce a local resistance in the sample region. The method also involves monitoring the photonic degradation of the sample region based on a photoluminescence measurement. The method also involves monitoring the local resistance of the sample region based on a sheet resistance measurement.

One or more embodiments are directed to calibrated, self-regulating, and high throughput systems for photovoltaic ultra-violet (UV) degradation testing. Embodiments may include implementation of a Real Time Ultra Violet Tester (RTUV Tester) to establish a direct, quantitative connection between the RTUV Photoluminescence (PL) signal and a local performance value (e.g., a performance value such as local resistance for a small location on a partially completed or completed solar cell). Such direct and quantitative calibration with local performance values can enable an in-process application of the RTUV, such as monitoring surface field UV stability in High Volume Manufacturing (HVM) and developing film stacks.

Processes described herein can be multiplexed and automated to deliver greater throughput as well as more consistent procedure and results. For example, by measuring multiple spots on a single cell or on a group of cells simultaneously, the throughput can be increased proportionately. In addition, the potential at a back surface of the cell can be fixed with an external supply, or using contactless light biasing, to provide more repeatable measurements. A secondary excitation source in the visible to near IR range can also be employed to provide a stronger PL signal. Such modifications may be implemented for in-line or end of line (EOL) monitoring with very high sampling rates for more effective screening and rapid feedback to process.

To provide context, for EOL UV testing, RTUV systems may be implemented to reduce EOL analysis time from 1-2 weeks down to 15 minutes. However, in order to further reduce such analysis time and allow for increased cell sampling rates, it may be necessary to greatly reduce the throughput of the system. In addition, other potential instabilities, such as the UV-LED light-source intensity, back contact potential, and temperature increases at the measurement spot may even lead to a reduced effectiveness of the RTUV measurement technique.

Addressing one of more of the above issues, in accordance with one or more embodiments of the present disclosure, one or more of the following is included in, or in conjunction with, a system for testing solar cell degradation to provide improvements over state pf the art real time UV degradation measurement systems: (1) UV power monitoring, (2) RTUV PL signal to local performance calibration, measured with both transient and steady-state signals for cross-corroboration, (3) modeling to guide and support the above calibration, (4) rapid feedback for in-process monitoring, local temperature monitoring by near IR (e.g., approximately 1100 nm) transmittance or conventional thermal (e.g., 2-10 micron) IR measurements, (5) the use of an additional light source for "reading" local performance such as a local resistance, (6) the use of an additional light source for mitigating or reducing a temperature or injection-level differential, (7) sub-bandgap lighting from rear to fill mid-level states, (8) external heating of a wafer to mitigate effects of localized heating, (9) the measurement of multiple spots on a wafer simultaneously and management of any potential crosstalk, (10) contact of a finished cell to monitor its voltage, and to maintain a constant voltage or current if needed, and/or (110automation and multiplexing.

To provide further context, UV power monitoring is accomplished with the use of a UV-sensitive detector positioned directly across from a source. Some of the UV light will penetrate a dichroic mirror, in a manner proportional to the principle beam. Alternatively, such a monitor can be placed below the mirror, or on the side of a lower column. It is to be appreciated that if the impinging UV light is too strong it may cause this monitor to degrade with time, in which case using a shutter to only measure this intensity periodically would be advantageous. In any case, the resulting signal can be used to feedback to the source to maintain constant power.

In a first aspect, multiple RTUV modules are included in one platform. Such an arrangement enables the measurement of several spots at once. Several such multi-spot RTUV stations can further be combined to increase throughput of a solar cell testing apparatus. Furthermore, automation may be implemented to directly unload, measure, and bin cells. The resulting increased throughput, when applied either at the EOL stage or during the fabrication process, can greatly reduce the time needed to feedback directly to process monitoring or development. As an exemplary system including multiple RTUV modules, FIG. 1 illustrates a schematic of a high throughput solar cell testing apparatus, in accordance with an embodiment of the present disclosure.

Referring to FIG. 1, a high throughput solar cell testing apparatus 100 includes a plurality of real time ultra-violet (RTUV) testing modules 102. Each of the RTUV testing modules 102 includes an ultra-violet (UV) light source, an optics assembly for focusing light from the UV light source on a sample area, and a detector for receiving photoluminescence energy from the sample area. The high throughput solar cell testing apparatus 100 also includes an acquisition and control assembly 104 coupled to the plurality of RTUV testing modules 102, and possibly further coupled to a software analysis and storage module 106. The system 100 may be suitable for testing either partially or completely fabricated solar cells, or both.

In an embodiment, the UV light source of each of the plurality of RTUV testing modules 102 includes a near UV light emitting diode (LED) having an output wavelength approximately in the range of 300-400 nanometers and, in a particular embodiment, having an output wavelength of approximately 365 nanometers. In an embodiment, the UV light source of each of the plurality of RTUV testing modules 102 includes a laser light source.

In an embodiment, the optics assembly of each of the plurality of RTUV testing modules 102 is arranged to provide a UV light spot on the sample area, the UV light spot having a relatively small dimension as compared to a tested solar cell, so as to not impact the performance of the solar cell. In an embodiment, the optics assembly of each of the plurality of RTUV testing modules 102 is arranged to provide a UV light spot on the sample area, the UV light spot having a dimension of less than approximately 2 millimeters. In a specific such embodiment, the UV light spot is approximately circular, and the dimension of less than approximately 2 millimeters is a diameter of the UV light spot. In another specific such embodiment, the UV light spot is approximately square, and the dimension of less than approximately 2 millimeters is a side of the UV light spot. In an embodiment, the detector for receiving photoluminescence energy from the sample area is an infra-red (IR) detector.

In an embodiment, each of the plurality of RTUV testing modules 102 includes an ambient light source, e.g., at approximately 660 nm, and is arranged to make pad contact for cell biasing. In one such embodiment, UV degradation is measured in each of the plurality of RTUV testing modules 102 under cell-biasing conditions. In on embodiment, an electrical vacuum chuck is used to hold and make contact to the cell. Different bias settings can be applied for creating varying effects on both signal strength and degradation strength.

In an embodiment, the high throughput solar cell testing apparatus 100 is arranged to provide automated insertion of solar cells from cassettes 108 through the plurality of RTUV testing modules 102 by a first conveyor belt 110. A second conveyor belt 112 send a tested solar cell into a pass cassette 114 or a fail cassette 116. It is to be appreciated that several features can be included in the system 100 to enable the monitoring and control of UV power by the software. For example, transient and steady-state RTUV signals can be measured and modeled to extract local resistance before and after of the UV test. In an embodiment, the system 100 further includes an electronic system coupled to the acquisition and control assembly. The electronic system is configured to determine whether to pass or fail a solar cell or a partially fabricated solar cell based on the photoluminescence energy detected by the detector of one or more of the plurality of RTUV testing modules. In other embodiments, electronic system is configured to determine how to bin or segregate tested solar cells based on the test results.

As described in greater detail below in association with FIGS. 3 and 4, one or more of the plurality of RTUV testing modules 102 further includes a sheet resistance measurement module coupled to the sample area. The sheet resistance measurement module is configured to measure a local resistance of a region of a solar cell or a partially fabricated solar cell in the sample area. In one such embodiment, the one or more of the plurality of RTUV testing modules 102 includes a visible light source separate and distinct from the UV light source. The visible light source is configured to provide visible light on the sample area for use in measuring the local resistance of the region of the solar cell or the partially fabricated solar cell in the sample area.

As described above, a plurality of RTUV modules can be included on a single platform to provide a high throughput testing system. As an example, of a suitable RTUV module, FIG. 2 illustrates a plan view of a solar cell testing apparatus, in accordance with another embodiment of the present disclosure.

Figure 2:
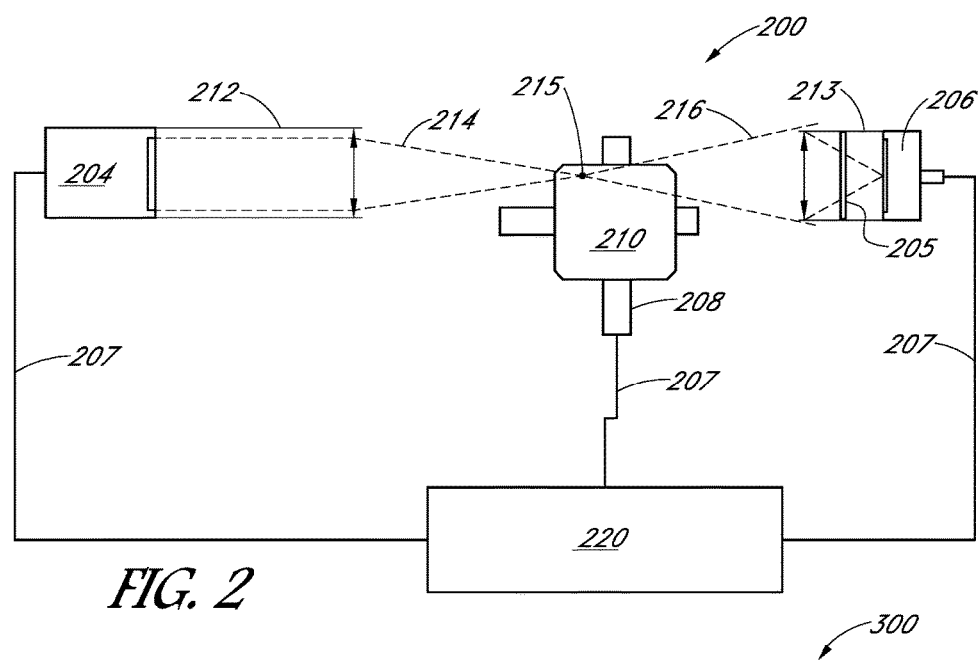
FIG. 2 illustrates a plan view of a solar cell testing apparatus, in accordance with another embodiment of the present disclosure.

Referring to FIG. 2, a solar cell testing apparatus 200 is shown for testing a solar cell 210, which may be a partially or completely fabricated solar cell. In an embodiment, the solar cell 210 has a front side opposite a back side of the solar cell 210. The solar cell 210 is placed on a receiving medium 208. In one embodiment, the receiving medium 208 is an electronic scanning and/or translator stage. The solar cell testing apparatus 200 includes a light source 204, which can include an optical tube 212 to focus light 214 from the light source 204 onto a location 215 of the solar cell 210. A photoluminescence signal 216 can be induced from the applied light 214 and received, obtained or collected from the solar cell 210.

In an embodiment, the photoluminescence signal 216 is received from the same location 215 as that focused on by the light 214 (e.g., as described in greater detail below in association with FIG. 5). The location 215 can be on the front side and/or back side of the solar cell 210. In one embodiment, the light source 204 is a laser or a light emitting diode (LED). In a specific embodiment, the light source 204 is a narrowband light source configured to induce photonic degradation to a solar cell, where the inducing includes applying light to the solar cell. In an embodiment, a detector 206 can be used to receive the photoluminescence signal 216 from the solar cell 210.

In an embodiment, a detector 206 is included and is positioned to receive the measured photoluminescence signal 216 induced from the applied light 214. In an embodiment, the detector 206 includes an optical tube 213 to collect the photoluminescence signal 216. In one embodiment, a filter 205 is used to remove or reduce noise from the photoluminescence signal 216.

In an embodiment, an electronic system 220 is connected 207 to the light source 204, detector 206 and the receiving medium 208. In one embodiment the electronic system 220 is used to modulate the light 214 from the light source 204.

In one embodiment, the electronic system 220 is used to monitor the photoluminescence signal 216 received at the detector 206 and record the photoluminescence signal 216. In one embodiment, the electronic system 220 is configured to monitor photonic degradation of a solar cell from the photoluminescence signal 216. In one embodiment, the electronic system 220 is configured to determine whether to pass or fail a solar cell based on the monitoring. In one embodiment, the electronic system 220 is used to control the movement of the receiving medium 208 (e.g., a scanning stage). In some embodiments, the light 214 is scanned along the surface of the solar cell 210. In one such embodiment, the light 214 is scanned along the front side and/or back side of the solar cell 210.

In an exemplary embodiment, the receiving medium 208 (e.g., a scanning stage) is used to move the location 215 from one location to another location on the solar cell 210. In one embodiment, the light 214 is scanned from one location on the solar cell to another location using galvanometric scanners. In an embodiment, a plurality of photoluminescence measurements received from scanning from one location to another location on the solar cell is used to generate a map, (e.g., a photonic degradation map) or other indicator of the degradation of the solar cell.

In an embodiment, the electronic system 220 includes an analog to digital converter (ADC), a current amplifier or pre-amplifier to boost, or a pico-ammeter to read the signal from the photoluminescence measurement. In an embodiment, the electronic system 220 includes an electronic control system to control the light from the light source 204 and/or to control the movement of the receiving medium 208 (e.g., a scanning stage). In some embodiments, additional electronics and/or software are incorporated into the electronic system 220.

Various components of the electronic system 220 and/or one or more portions of the disclosed techniques can be implemented by a processor unit executing program instructions stored on a memory. In various embodiments, the processor unit can include one or more processors or cores. The processor unit can contain a cache or other form of on-board memory. The memory is usable by the processor unit (e.g., to store instructions executable by and data used by the processor unit). The memory can be implemented by any suitable type of physical memory media, including hard disk storage, floppy disk storage, removable disk storage, flash memory, random access memory (RAM-SRAM, EDO RAM, SDRAM, DDR SDRAM, Rambus® RAM, etc.), ROM (PROM, EEPROM, etc.), and so on. The memory can consist solely of volatile memory in one embodiment. The circuitry can include an I/O interface configured to couple to and communicate with other devices (e.g., to receive a value representing the threshold voltage), according to various embodiments.

Articles of manufacture that store instructions (and, optionally, data) executable by a computer system to implement various techniques disclosed herein are also contemplated. These articles of manufacture include tangible computer-readable memory media. The contemplated tangible computer-readable memory media include portions of the memory subsystem of a computer system (without limitation SDRAM, DDR SDRAM, RDRAM, SRAM, flash memory, and various types of ROM, etc.), as well as storage media or memory media such as magnetic (e.g., disk) or optical media (e.g., CD, DVD, and related technologies, etc.). The tangible computer-readable memory media may be either volatile or nonvolatile memory.

In another aspect, calibration to resistance of both the RTUV steady state and transient signal is performed. Such testing can allow for a direct correlation of the measured signal to cell performance. For example, local temperature measurement (e.g., utilizing IR transmittance at approximately 1100 nm) or a conventional thermal IR measurement can be obtained to test for the effects of a local temperature increase on the PL signal. Use of additional lighting and/or higher base temperature of the cell can be included in an RTUV module to mitigate any effects from such temperature change. In an embodiment, in order to increase signal strength, a secondary excitation beam in the visible to near IR is further included in the RTUV module. In addition, by making electrical contact to the cell and holding it in forward bias, the PL signal may be increased by several orders of magnitude. In another embodiment, an external light source of a relatively longer wavelength is included. In another embodiment, the cell is illuminated from either the front or back with a sub-bandgap light to reduce noise.

As described above, a plurality of RTUV modules can be included on a single platform to provide a high throughput testing system. As an example, of a suitable RTUV module which has a capability measuring the local resistance of the region of the solar cell, FIG. 3 illustrates a cross-sectional view of a solar cell testing apparatus, in accordance with another embodiment of the present disclosure.

Figure 3:
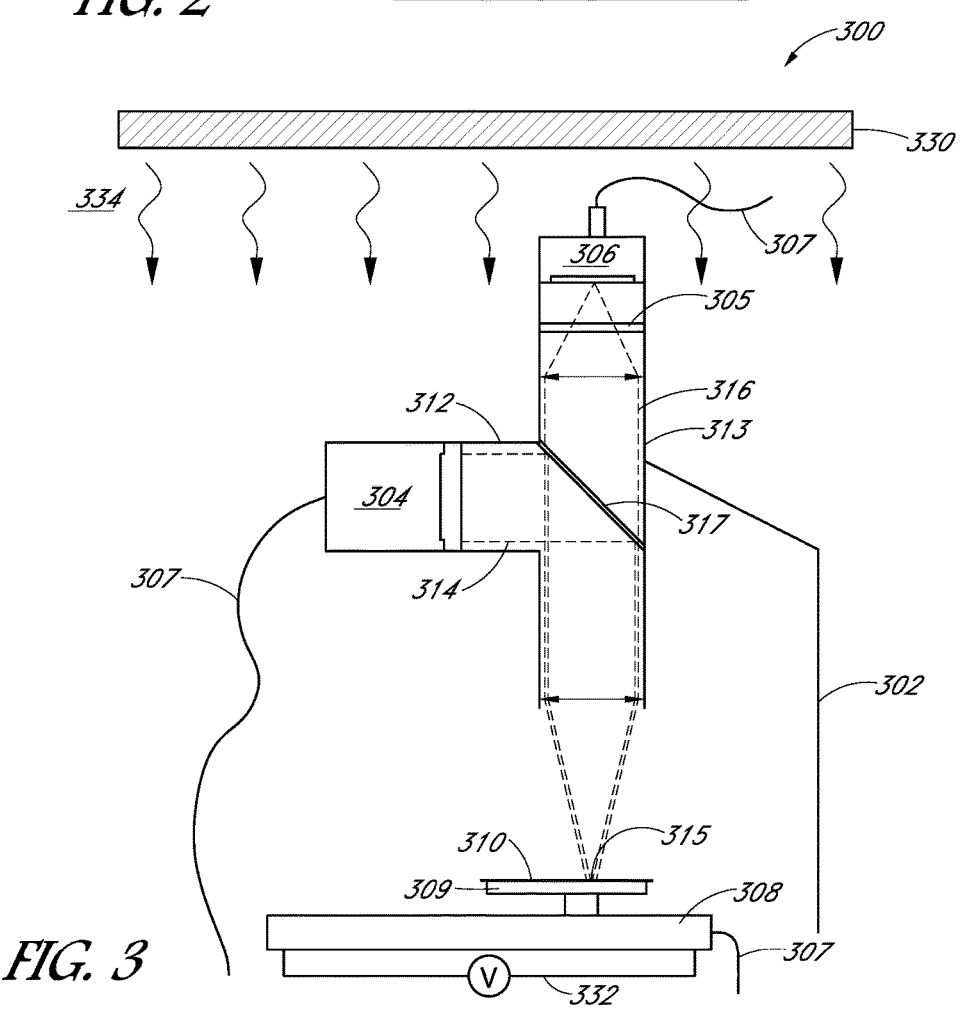
FIG. 3 illustrates a cross-sectional view of a solar cell testing apparatus, in accordance with another embodiment of the present disclosure.
Figure 4:
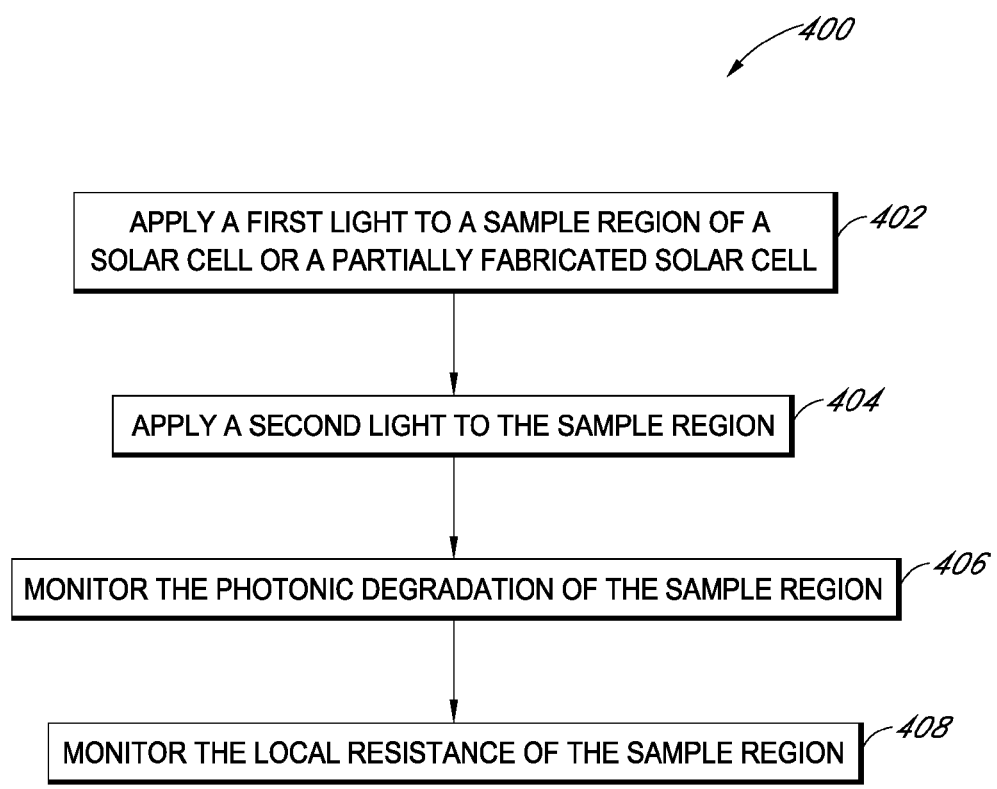
FIG. 4 is a flowchart listing operations in a method of testing a solar cell, in accordance with an embodiment of the present disclosure.

Referring to FIG. 3, a solar cell testing apparatus 300 is shown for testing a solar cell 310, which may be a partially or completely fabricated solar cell. The solar cell testing apparatus 300 includes a light source 304. The light source 304 includes an optical tube 312 to focus light 314 from the light source 304 onto a location 315 of the solar cell 310. In an embodiment, a photoluminescence signal 316 induced from the applied light 314 is received from the solar cell 310. In one such embodiment, the photoluminescence signal 316 is received from the same location 315 as that focused on by the light 314. The location 315 can be on the front side and/or back side of the solar cell 310. In an embodiment, the light source 304 is a laser or a light emitting diode (LED). A detector 306 is used to receive the photoluminescence signal 316 from the solar cell 310.

In an embodiment, the light 314 is co-axial, e.g., the light 314 in the same optical axis as that of the photoluminescence signal 316, as depicted in FIG. 3. In one embodiment, light from a narrowband light source and the measured photoluminescence 316 are at least partially co-axial. In an embodiment, a dichroic mirror 317 is used to separate the light 314 and the photoluminescence signal 316. In one embodiment, the dichroic mirror 317 is used to separate light from a narrowband light source and the measured photoluminescence 316. In one embodiment, the detector 306 further includes an optical tube 313 to collect the photoluminescence signal 316. In one embodiment, a filter 305 is used to remove or reduce the source illumination (e.g., light 314) and/or background noise from the photoluminescence signal 316.

In an embodiment, the solar cell testing apparatus 300 includes a second light source 330. In one embodiment, the second light source 330 provides a light 334. In one embodiment, the second light source 330 is a narrowband light source. In a specific such embodiment, the second light source 330 is a visible light source, e.g., a red light source provides light 334 at approximately 660 nm. In one embodiment, the second light source 330 is a flooding light LED array.

In an embodiment, the second light source 330 is used together with or as part of a sheet resistance measurement module. In one such embodiment, the sheet resistance measurement module further includes a source meter 332. In an embodiment, the sheet resistance measurement module does not include additional optics and is based on a flooding second light source 330, as depicted. In another embodiment, however, the second light source 330 is further coupled to an optics assembly for focusing light from the narrowband light source 330 on a sample area of a solar cell or a partially fabricated solar cell. In either case, in an embodiment, the second light source 330 provides light 334 and is used together with the source meter 332 to provide capability for local resistance measurements.

In an embodiment, an electronic system (not shown), similar to the electronic system described in association with FIG. 2, is connected 307 to the light source 304, detector 306 and receiving medium 308. In one embodiment, the electronic system is used to modulate the light 314 from the light source 304. In one embodiment, the electronic system is used to monitor the photoluminescence signal 316 received at the detector 306 and record the photoluminescence signal 316. In one embodiment, the electronic system is configured to monitor photonic degradation of a solar cell from the photoluminescence signal 316. In one embodiment, the electronic system is configured to determine whether to pass or fail a solar cell based on the monitoring. In one embodiment, the photoluminescence signal 316 is used to determine the induced degradation to solar cell 310. In one embodiment, the electronic system is used to control the movement of the receiving medium (e.g., a scanning stage) 308. In an embodiment, the receiving medium 308 is an electronic scanning and/or translator stage. In one embodiment, the receiving medium 308 further includes a chuck 309, where the solar cell 310 is placed on the chuck 309. In an embodiment, the front and/or back side of the solar cell 310 is in contact with the chuck 309. In an embodiment, a mount 302 is used to support the solar cell testing apparatus 300. In some embodiments, the light 314 is scanned along the surface of the solar cell 310. In an embodiment, the light 314 is scanned along the front side and/or back side of the solar cell 310.

In an exemplary embodiment, the receiving medium 308 (e.g., a scanning stage) is used to move the location 315 from one location to another location on the solar cell 310. In one embodiment, the light 314 is scanned from one location on the solar cell to another location using galvanometric scanners. In an embodiment, a plurality of photoluminescence measurements received from scanning from one location to another location on the solar cell is used to generate a map, (e.g., a photonic degradation map) or other indicator of the degradation of the solar cell.

Thus, referring again to FIG. 3, in accordance with an embodiment of the present disclosure, a solar cell testing apparatus 300 includes a first narrowband light source 304 configured to induce photonic degradation to a solar cell 310. The inducing includes applying light 314 of a first wavelength to the solar cell 310. A second narrowband light source 330 is included for applying light 334 of a second wavelength to the solar cell 310. The second wavelength is greater than the first wavelength. A detector 306 is included and is configured to measure photoluminescence induced from the applied light 314 of the first wavelength. A sheet resistance measurement module 332 is included and is configured to measure a local resistance of a region of the solar cell 310. In one embodiment, an electronic system (, such as or similar to electronic system 220) is included and is configured to monitor the photonic degradation of the solar cell 310 from the photoluminescence measurement, and is further configured to monitor the local resistance of the region of the solar cell 310.

In an embodiment, the first narrowband light source 304 is a UV light source, and the second narrowband light source 330 is a visible light source. In one such embodiment, the UV light source 304 includes a near UV light emitting diode (LED) having an output wavelength of approximately 365 nanometers, and the visible light source 330 is a red light source, e.g., having a wavelength of approximately 660 nm.

In an embodiment, the solar cell testing apparatus 300 further includes an optics assembly for focusing light from one of the first narrowband light source or the second narrowband light source on a sample area of a solar cell or a partially fabricated solar cell. In one such embodiment, the optics assembly is configured to provide a light spot on the sample area, the light spot having a dimension of less than approximately 2 millimeters. In a specific such embodiment, the light spot is approximately circular, and the dimension of less than approximately 2 millimeters is a diameter of the light spot. In another specific such embodiment, the light spot is approximately square, and the dimension of less than approximately 2 millimeters is a side of the light spot.

In another aspect, methods are described for monitoring both a photoluminescence measurement and a sheet resistance measurement. As an example, FIG. 4 is a flowchart 400 listing operations in a method of testing a solar cell, in accordance with an embodiment of the present disclosure.

Referring to operation 402 of flowchart 400, a method for testing a solar cell involves applying a first light to a sample region of a solar cell or a partially fabricated solar cell to induce a photonic degradation in the sample region. Referring to operation 404 of flowchart 400, a second light is applied to the sample region to induce a local resistance in the sample region. Referring to operation 406 of flowchart 400, the photonic degradation of the sample region is monitored based on a photoluminescence measurement. Referring to operation 408 of flowchart 400, the local resistance of the sample region is monitored based on a sheet resistance measurement.

In an embodiment, monitoring the photonic degradation of the sample region is performed at substantially the same time as monitoring the local resistance of the sample region. In an embodiment, applying the first light involves applying UV light. Applying the second light involves applying visible light.

In an embodiment, the above described method is performed at multiple locations of a solar cell to induce degradation at multiple locations of the solar cell and receive multiple corresponding photoluminescence measurements. In an example, the light can be applied to a plurality of locations on a front side of a solar cell opposite to a plurality of contact pads formed on a back side of the solar cell. Corresponding induced photoluminescence measurements are obtained. In an embodiment, a plurality of photoluminescence measurements is to generate a map (e.g., a photonic degradation map) or other indicator of ultraviolet (UV) induced degradation of the solar cell. In one such embodiment, the induced photonic degradation of the solar cell is monitored during fabrication or after fabrication based on the photonic degradation map.

To provide further context, the capability to measure degradation in an accelerated manner can be crucial to improving a solar cell performance and reliability of the solar cell in the field. For example, photonic induced degradation (e.g., degradation from specific wavelengths of light) can deteriorate the performance of a solar cell over time. In a specific example, ultraviolet (UV) induced degradation can deteriorate the performance of a solar cell out in the field. Thus, specific test methods may be desirable to determine if solar cells are susceptible to ultraviolet (UV) induced degradation during manufacture or prior to product shipment to prevent product which is susceptible to ultraviolet (UV) induced degradation from reaching the customer or installation in the field. The longevity of a solar cell or solar cell module can directly affect the value of the product to a customer and the product's competitiveness in the marketplace. Also, the rapid pace of solar cell process development and qualification can require a high acceleration factor (AF), e.g., to have test results available in a timely manner for use and/or feedback to the solar cell manufacturing process.

Using a broadband source of light, such as a mercury lamp, may have the disadvantage of exposing the solar cell to a broad spectrum of light. In an example, a mercury lamp can emit irradiance in the ultraviolet (UV), visible, and infrared (IR) spectral range. Also, the amount of ultraviolet (UV) light emitted by the mercury lamp can be limited. In one example, long exposure times from a mercury lamp are required to induce similar ultraviolet (UV) degradation a solar cell would undergo from ultraviolet (UV) light exposure in the field. In addition, the spectrum of the mercury lamp contains many spikes and the intensities of these spikes are known to vary, either from lamp to lamp or over time. Such variations can be a source of inconsistency and/or uncertainty for use in ultraviolet (UV) testing.

In an embodiment, using light from a narrowband source (e.g., using a laser or a light emitting diode (LED)) allows for reduced exposure times in comparison to using light from a broadband source (e.g., using mercury lamps can take several days or weeks). In an embodiment, a narrowband source can include one or more of the wavelength groups: 101-280 nm, 280-315 nm, or 315-400 nm (corresponding to the ultraviolet (UVA-UVC) wavelength range), 400-500 nm, 500-600 nm, or 600-700 nm (corresponding to the visible range), and 700-800 nm, 800-900 nm, 900-1000 nm (corresponding to the near infrared (IR) wavelength range). In an embodiment, the light is applied for less than a second to induce degradation on the solar cell. In one embodiment, the light is applied to the solar cell up to 1-2 hours or more to induce photonic degradation. In an embodiment, light is applied to the solar cell for a duration in the range of 10 milliseconds-2 hours to induce photonic degradation.

In an embodiment, the light is applied to a passivation region of the solar cell, e.g., an anti-reflective region (AR) of the solar cell. In one such embodiment, the passivation region is on a front side and/or a back side of the solar cell. In a specific embodiment, the light is applied to a passivation region on the front side of the solar cell opposite to a contact region on a back side of the solar cell (e.g., as shown in FIG. 5, described below). In an embodiment, the light is applied to one or more locations of the solar cell.

In an example, the light may be applied to one or more locations on the front side of the solar cell opposite to one or more contact regions on a back side of the solar cell. FIG. 5 illustrates a cross-sectional view of an operation involving applying light to a solar cell, in accordance with an embodiment of the present disclosure.

Figure 5:
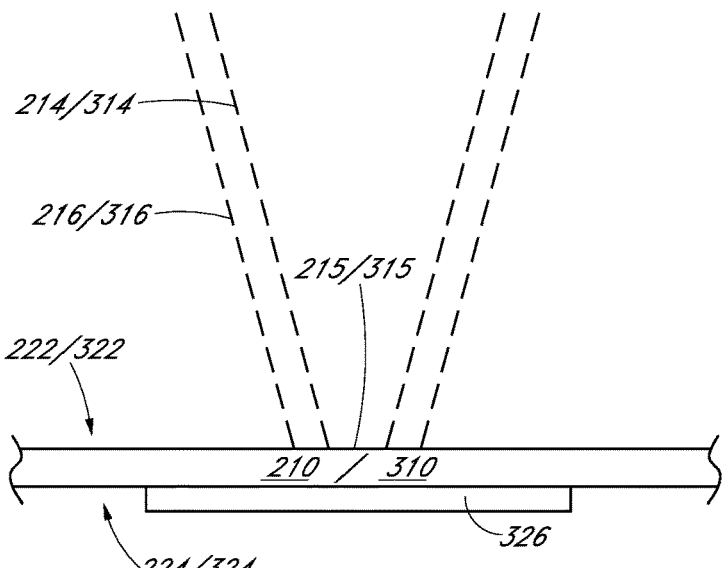
FIG. 5 illustrates a cross-sectional view of an operation involving applying light to a solar cell, in accordance with an embodiment of the present disclosure.

Referring to FIG. 5, light is applied to a solar cell, which may be a partially or completely fabricated solar cell, to induce degradation. In the example, the solar cell 210/310 has a front side 222/322 opposite a back side 224/324. Light 214/314 is applied to a location 215/315 of solar cell 210/310 to induce a photoluminescence 216/316. A photoluminescence signal 216/316 can be received from the location 215/315 (e.g., the same location the light 214/314 is applied). In an embodiment, the location 215/315 is on a front side 222/322 of the solar cell 210/310. In an embodiment, the location 215/315 is opposite to a contact region 326 on a back side 224/324 of the solar cell 210/310. In one embodiment, the contact region 326 is a contact pad. In one embodiment, the location 215/315 is a passivation region (e.g., a silicon dioxide layer and/or a silicon nitride layer) of a solar cell.

Other approaches may also induce degradation. As an example, FIG. 6 illustrates a cross-sectional view of an operation involving applying light to a solar cell, in accordance with another embodiment of the present disclosure.

Figure 6:
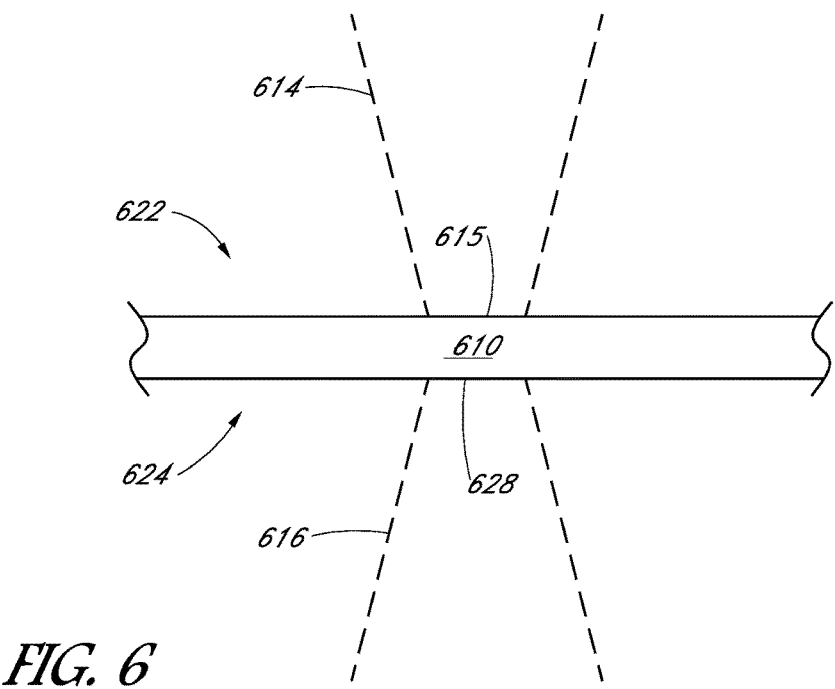
FIG. 6 illustrates a cross-sectional view of an operation involving applying light to a solar cell, in accordance with another embodiment of the present disclosure.

Referring to FIG. 6, a solar cell 610 (which may be a partially or completely fabricated solar cell) has a front side 622 opposite a back side 624. Light 614 is applied to a location 615 on the front side 622 of the solar cell 610 to induce a photoluminescence 616. A photoluminescence signal 616 can be received from another location 628 on the back side 624 of the solar cell 610. In one embodiment, the location 615 is a passivation region (e.g., a silicon dioxide layer and/or a silicon nitride layer) of a solar cell.

In an embodiment, a light source is positioned to face the front side 622 in order to provide light 614 to the front side 622 of the solar cell 610. A detector is positioned to face the back side 624 to receive the photoluminescence signal 616 from the back side 624 of the solar cell 610.

In an aspect, degradation of a solar cell can be monitored based on at least a photoluminescence measurement. In an embodiment, such monitoring includes receiving a first photoluminescence measurement induced from an applied light and receiving a second photoluminescence measurement induced from the applied light (e.g., light from the same source) after receiving the first photoluminescence measurement. In an example, light illuminating a solar cell can generate electron and hole pairs. At steady state, the density of the generated electron and hole pairs depend on the passivation of the solar cell. Under equal illumination, for a solar cell with good passivation (e.g., low surface recombination), the higher the generated electron and hole density, the higher the photoluminescence intensity. In an embodiment, reduced photoluminescence intensity is used to indicate degradation in a passivation region of the solar cell. Thus, monitoring the measured change of the photoluminescence intensity under constant illumination can be used to determine the change in a passivation (e.g., induced degradation) of a solar cell. In one embodiment, the surface recombination of the solar cell is measured using the photoluminescence intensity.

Figure 7:
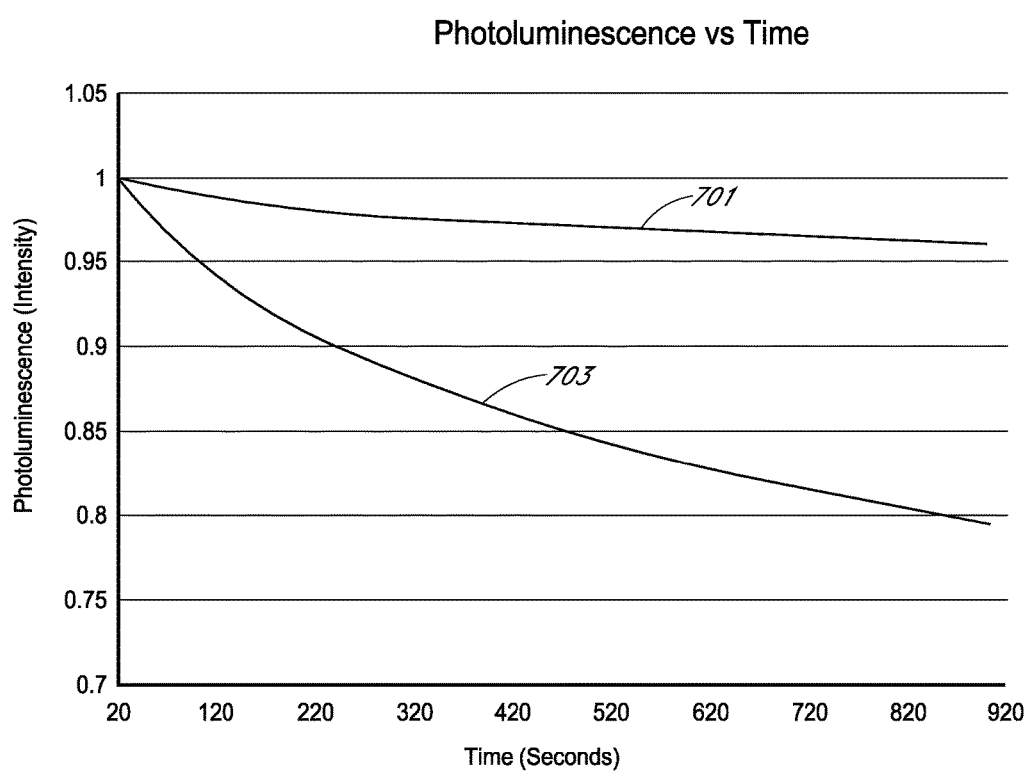
FIG. 7 illustrates exemplary data plotted for photoluminescence as a function of time, in accordance with an embodiment of the present disclosure.

As exemplary PL information, FIG. 7 illustrates exemplary data plotted for photoluminescence as a function of time, in accordance with an embodiment of the present disclosure.

Referring to FIG. 7, photoluminescence data is normalized to simplify presentation of the data. In particular, two photoluminescence measurements, 701 and 703 are shown in FIG. 7, as taken from a solar cell which may be a partially or completely fabricated solar cell. In one example, the measurements are taken during exposure to ultraviolet (UV) light. In another example, the measurements are taken after applying ultraviolet (UV) light. As shown, measurement 703 illustrates an approximately 20% reduction in photoluminescence over time (e.g., over 900 seconds). Measurement 701 shows less than 5% reduction in the photoluminescence measurement over the same duration. In the example shown, a deterioration, e.g., greater than 5% photoluminescence loss, can be defined as a fail and the ultraviolet (UV)

degradation of that solar cell determined to be unacceptable. Thus, in the same example, measurement 701 can be acceptable (passing solar cell) and measurement 703 can correspond to a failing solar cell. Although one example is presented herein, other example configurations and/or measurements may be used.

Embodiments described herein may be implemented to enable much faster UV degradation measurements and/or more rapid (if EOL) or nearly instantaneous (if in-line) feedback to process and/or enable greater sampling rates. Although certain modules or materials are described specifically with reference to above described embodiments, some modules or materials may be readily substituted with others with such embodiments remaining within the spirit and scope of embodiments of the present disclosure. Embodiments disclosed herein may be suitable for solar cells based on a silicon substrate or solar cells based on a different material substrate, such as a group III-V material substrate. Embodiments disclosed herein may be suitable for solar cells having back side alternating N+ type and P+ type emitter regions, or for other solar cell arrangements, such as front contact solar cell arrangements. In other embodiments, the above described approaches can be applicable to manufacturing of articles other than solar cells. For example, manufacturing of light emitting diode (LEDs) may benefit from approaches described herein. Furthermore, although applying ultraviolet (UV) light to induce ultraviolet (UV) degradation is described herein, other light sources and degradation modes can be applied and/or induced within the spirit and scope of embodiments contemplated for the present disclosure.

As described above, the local resistance of a sample region may be monitored based on a sheet resistance measurement made at the same time or substantially the same time as a photoluminescence measurement. In one such embodiment, a non-contact measurement of front surface sheet resistance of textured solar wafers is performed using a narrow band light source while simultaneously measuring photoluminescence. It is to be appreciated that, in other embodiments, a standalone sheet resistance measurement may be made and/or a system can include a stand-alone sheet resistance measurement module.

In an embodiment, the monitoring of a front surface sheet resistance is improved by enabling the measurement of textured cells through a non-contact technique. In one such embodiment, actual product wafers (or partially fabricated product wafers) are tested instead of, e.g., polished test wafers. Furthermore, in an embodiment, such an approach enables the testing of larger sample sizes at a speed suitable for inline measurement. Embodiments described herein may be implemented to enable very high detection of bad or faulty cells, reducing field failures.

To provide context, front surface phosphorous doping of solar cells may be critical to ensuring stable performance under ultra-violet (UV) exposure in the field. Insufficient front surface doping is understood to be one cause of field returns related to cell defects. Not to be bound by theory, there may be at least a couple of reasons numerous problematic cells reaching the field: (1) Product cells are typically not measured for sheet resistance. Special polished test wafers are typically measured using a four-point probe. The test wafers do not undergo all processing operations to which product wafers are exposed. Accordingly, test wafers may not be exposed to the very causes of high sheet resistance possibly observed in product wafers. (2) The sample size is small.

Addressing one or more of the above issues, in accordance with an embodiment of the present disclosure, a narrow band light source is used that is absorbed near the surface of silicon (Si) to generate a photo-luminescence signal that can be correlated to the sheet resistance or doping concentration of the surface. It is to be appreciated that, in one embodiment, the wavelength used does not damage the wafer but instead is absorbed close to the surface of the wafer. The intensity of the light may not be critical, however, high intensity light may heat the wafer surface and require more stabilization time. As such, in one embodiment, a relatively low intensity light source is used to provide a high throughput measurement. In one particular embodiment, one large flash is used as an illumination event. In another particular embodiment, small points of light are used as an illumination event to map the surface.

In an exemplary embodiment, a photoluminescence (PL) signal obtained at t=5s from an infra-red (IR) detector correlates to sheet rho (sheet resistance). PL output is measured for multiple spots across the wafer and then averaged for a final resistance value for the cell. In a particular embodiment, a 365 nm LED light source is used. In a particular embodiment, cells are sampled as partially fabricated cells following a front side dopant drive, such as a front-side phosphorous dopant drive.

Thus, high throughput systems for photovoltaic UV degradation testing of solar cells, and methods of testing for UV degradation of solar cell during manufacture, have been disclosed.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of the present disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of the present application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A high throughput solar cell testing apparatus, comprising:
   a plurality of real time ultra-violet (RTUV) testing modules, each of the RTUV testing modules comprising:
      an ultra-violet (UV) light source;
      an optics assembly for focusing light from the UV light source on a sample area; and
      a detector for receiving photoluminescence energy from the sample area; and
   an acquisition and control assembly coupled to the plurality of RTUV testing modules.

2. The testing apparatus of claim 1, wherein the UV light source of each of the plurality of RTUV testing modules comprises a near UV light emitting diode (LED) having an output wavelength approximately in the range of 300-400 nanometers.

3. The testing apparatus of claim 1, wherein the optics assembly of each of the plurality of RTUV testing modules is configured to provide a UV light spot on the sample area, the UV light spot having a dimension of less than approximately 2 millimeters.

4. The testing apparatus of claim 3, wherein the UV light spot is approximately circular, and the dimension of less than approximately 2 millimeters is a diameter of the UV light spot.

5. The testing apparatus of claim 3, wherein the UV light spot is approximately square, and the dimension of less than approximately 2 millimeters is a side of the UV light spot.

6. The testing apparatus of claim 1, wherein the detector for receiving photoluminescence energy from the sample area is an infra-red (IR) detector.

7. The testing apparatus of claim 1, further comprising:
an electronic system coupled to the acquisition and control assembly, the electronic system configured to determine whether to pass or fail a solar cell or a partially fabricated solar cell based on the photoluminescence energy detected by the detector of one or more of the plurality of RTUV testing modules.

8. The testing apparatus of claim 1, wherein one or more of the plurality of RTUV testing modules further comprises:
a sheet resistance measurement module coupled to the sample area, the sheet resistance measurement module configured to measure a local resistance of a region of a solar cell or a partially fabricated solar cell in the sample area.

9. The testing apparatus of claim 8, wherein the one or more of the plurality of RTUV testing modules comprises a visible light source separate and distinct from the UV light source, and wherein the visible light source is configured to provide visible light on the sample area for use in measuring the local resistance of the region of the solar cell or the partially fabricated solar cell in the sample area.

10. A solar cell testing apparatus, comprising:
a first narrowband light source configured to induce photonic degradation to a solar cell, wherein the inducing includes applying light of a first wavelength to the solar cell;
a second narrowband light source for applying light of a second wavelength to the solar cell, the second wavelength greater than the first wavelength;
a detector configured to measure photoluminescence induced from the applied light of the first wavelength;
a sheet resistance measurement module configured to measure a local resistance of a region of the solar cell; and
an electronic system configured to monitor the photonic degradation of the solar cell from the photoluminescence measurement, and configured to monitor the local resistance of the region of the solar cell.

11. The solar cell testing apparatus of claim 10, wherein the first narrowband light source is a UV light source, and the second narrowband light source is a visible light source.

12. The solar cell testing apparatus of claim 11, wherein the UV light source comprises a near UV light emitting diode (LED) having an output wavelength of approximately 365 nanometers, and the visible light source is a red light source.

13. The solar cell testing apparatus of claim 10, wherein the electronic system is configured to determine whether to pass or fail a solar cell or a partially fabricated solar cell based on the monitoring.

14. The solar cell testing apparatus of claim 10, further comprising:
an optics assembly for focusing light from one of the first narrowband light source or the second narrowband light source on a sample area of a solar cell or a partially fabricated solar cell.

15. The testing apparatus of claim 14, wherein the optics assembly is configured to provide a light spot on the sample area, the light spot having a dimension of less than approximately 2 millimeters.

16. The testing apparatus of claim 15, wherein the light spot is approximately circular, and the dimension of less than approximately 2 millimeters is a diameter of the light spot.

17. The testing apparatus of claim 15, wherein the light spot is approximately square, and the dimension of less than approximately 2 millimeters is a side of the light spot.

18. A method for testing a solar cell, the method comprising:
applying a first light to a sample region of a solar cell or a partially fabricated solar cell to induce a photonic degradation in the sample region;
applying a second light to the sample region to induce a local resistance in the sample region;
monitoring the photonic degradation of the sample region based on a photoluminescence measurement; and
monitoring the local resistance of the sample region based on a sheet resistance measurement.

19. The method of claim 18, wherein monitoring the photonic degradation of the sample region is performed at substantially the same time as monitoring the local resistance of the sample region.

20. The method of claim 18, wherein applying the first light comprises applying UV light, and applying the second light comprises applying visible light.

* * * * *